(12) United States Patent
Hamza et al.

(10) Patent No.: US 6,291,820 B1
(45) Date of Patent: Sep. 18, 2001

(54) HIGHLY CHARGED ION SECONDARY ION MASS SPECTROSCOPY

(75) Inventors: Alex V. Hamza, Livermore; Thomas Schenkel, San Francisco; Alan V. Barnes; Dieter H. Schneider, both of Livermore, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/227,997

(22) Filed: Jan. 8, 1999

(51) Int. Cl.[7] .............................. B01D 59/44; H01J 49/00
(52) U.S. Cl. ..................... 250/282; 250/287; 250/309
(58) Field of Search .................................. 250/309, 287, 250/282

(56) References Cited

PUBLICATIONS

Beam Interactions with Materials & Atoms, T. Schenkel et al., Nuclear Instruments and Methods in Physics Research B 125 (1997) 153–158.
Emission of Secondary Particles from Metals and Insulators at Impact of Slow Highly Charged Ions, T. Schenkel et al., Nuclear Instruments and Methods in Physics Research B 00 (1996) 1–6.
Electronic Sputtering of Thin Conductors by Neutralization of Slow Highly Charged Ions, T. Schenkel et al., The American Physical Society (1997) 1–4.
Electronic Sputtering and Desorption Effects in TOF–SIMS Studies Using Slow Highly Charged Ions Like AU$^{69+}$, T. Schenkel et al., Materials Science Applications of Ion Beam Techniques, (1997) 1–5.
Quantification of Metal Trace Contaminants on Wi Wafer Surfaces by Laser–SNMS and TOF–SIMS Using Sputter Deposited Submonolayer Standards, A. Schnieders et al., American Vacuum Society, (1996) 2712–2724.
McGraw–Hill Yearbook of Science & Technology, (1996) 25–29.
The Electron–Beam Ion Trap, Roscoe E. Marrs et al., American Institute of Physics, Oct. (1994) 27–34.

*Primary Examiner*—Jack Berman
*Assistant Examiner*—Kalimah Fernandez
(74) *Attorney, Agent, or Firm*—Alan H. Thompson; L. E. Carnahan

(57) ABSTRACT

A secondary ion mass spectrometer using slow, highly charged ions produced in an electron beam ion trap permits ultra-sensitive surface analysis and high spatial resolution simultaneously. The spectrometer comprises an ion source producing a primary ion beam of highly charged ions that are directed at a target surface, a mass analyzer, and a microchannel plate detector of secondary ions that are sputtered from the target surface after interaction with the primary beam. The unusually high secondary ion yield permits the use of coincidence counting, in which the secondary ion stops are detected in coincidence with a particular secondary ion. The association of specific molecular species can be correlated. The unique multiple secondary nature of the highly charged ion interaction enables this new analytical technique.

3 Claims, 3 Drawing Sheets

HIGHLY CHARGED ION SECONDARY ION MASS SPECTROSCOPY

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to secondary ion mass spectrometry using slow, highly charged ions.

2. Description of Related Art

The requirements on surface analytical techniques are becoming more stringent, particularly as the feature size of semiconductor devices continues to decrease. Among the currently available techniques, secondary ion mass spectroscopy (SIMS) is highly favored because it offers in-depth information, low detection limits, and high depth resolution. In standard SIMS, a primary beam of energetic singly charged ions strikes a sample surface, which releases electrons and secondary ions. Typically, the sputter yield is about 2–10 sample atoms per incident ion, and the secondary ion yield per incident ion is often less than $10^{-2}$. The number of secondary ion counts per unit of sample consumption primarily determines the sensitivity limit of SIMS. In the case of surface analysis by static SIMS, values for sensitivity limits are on the order of $10^9$ atoms/cm$^2$.

The atomic and molecular secondary ions emanating from the sample are introduced into a mass analyzer; both positive and negative ion mass spectra of the species present in the surface can be measured. While the molecular ions can dissociate, these fragment ions are usually not distinguished and give rise to some background. The SIMS spectrum contains secondary ions that are stable to dissociation and the ionic fragments of those that are not. The composition of a microscopic region on the surface of the solid sample can thus be elucidated. Instruments for conducting SIMS are broadly classified into two types: a scanning type that scans an analyzed region with a sharply focused primary beam to obtain an ion image, and a direct imaging type that bombards the whole analyzed region with a primary beam of a relatively large diameter and obtains an ion image on the principle of an ion microscope.

Limitations in standard SIMS are becoming apparent in more advanced applications. Development of the next generations of semiconductor devices will require much improved characterization techniques. Thus, a need exists to develop SIMS with at least an order of magnitude greater sensitivity. The present invention addresses the limitations of conventional SIMS by using enhanced sputtering by slow, highly charged ions.

SUMMARY OF THE INVENTION

The present invention is a secondary ion mass spectrometry system using slow, highly charged ions. The system comprises a ion source producing a primary ion beam of highly charged ions (HCI), which are directed at a target surface, and a time-of-flight mass analyzer and a detector of the secondary ions that are sputtered from the target surface after interaction with the primary beam. Highly charged ions create extreme densities of electronic excitations on surfaces; thus, yields of secondary ions per incident ion are increased by two to three orders of magnitude compared to singly charged ions, which allows a 10 to 100-fold improvement in the sensitivity of the quantitative surface analysis. Examples of highly charged ions include $Xe^{12-52+}$ and $Au^{44-69+}$.

The present invention further improves on standard SIMS by applying coincidence counting. The high secondary ion yield and the secondary ion emission from a small area as a result of HCI-SIMS make the coincidence technique very powerful. In coincidence counting, the secondary ion stops are detected in coincidence with a start signal. There may be the additional requirement that a particular secondary ion is present. To detect secondary ions in coincidence with a required secondary ion on a practical time scale (e.g., hours vs. days), the secondary ion yield must be on the order produced by HCI-SIMS, i.e., 1–20 secondary ions per primary ion, in contrast with conventional SIMS, which on average provides less than 0.01 secondary ions per primary ion. Highly charged ion excitation is well suited to coincidence time-of-flight secondary ion mass spectrometry.

The present invention offers high mass resolution and mass accuracy for surface characterization and unambiguous identification of organic compounds and inorganic elemental contamination on surfaces, in particular, the quantification of metal trace contaminants on silicon wafer surfaces. The present invention is useful for determining dopant concentrations in semiconductor materials. In addition, HCI-SIMS is extremely surface sensitive and analyzes over a mass range of one to >3000 amu. The high potential energy excitation in the surface by the highly charged ions leads to the desorption of molecular cluster ions. HCI-SIMS is a novel cluster source and enables the investigation of cluster stability of a large number of materials. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention is a secondary ion mass spectrometer using slow, highly charged ions produced in an electron beam ion trap. The spectrometer comprises an ion source producing a primary ion beam of highly charged ions that are directed at a target surface, and a microchannel plate detector of secondary ions that are sputtered from the target surface after interaction with the primary beam. The use of highly charged ions (HCI) permits ultra-sensitive surface analysis and high spatial resolution simultaneously.

Figure 1:
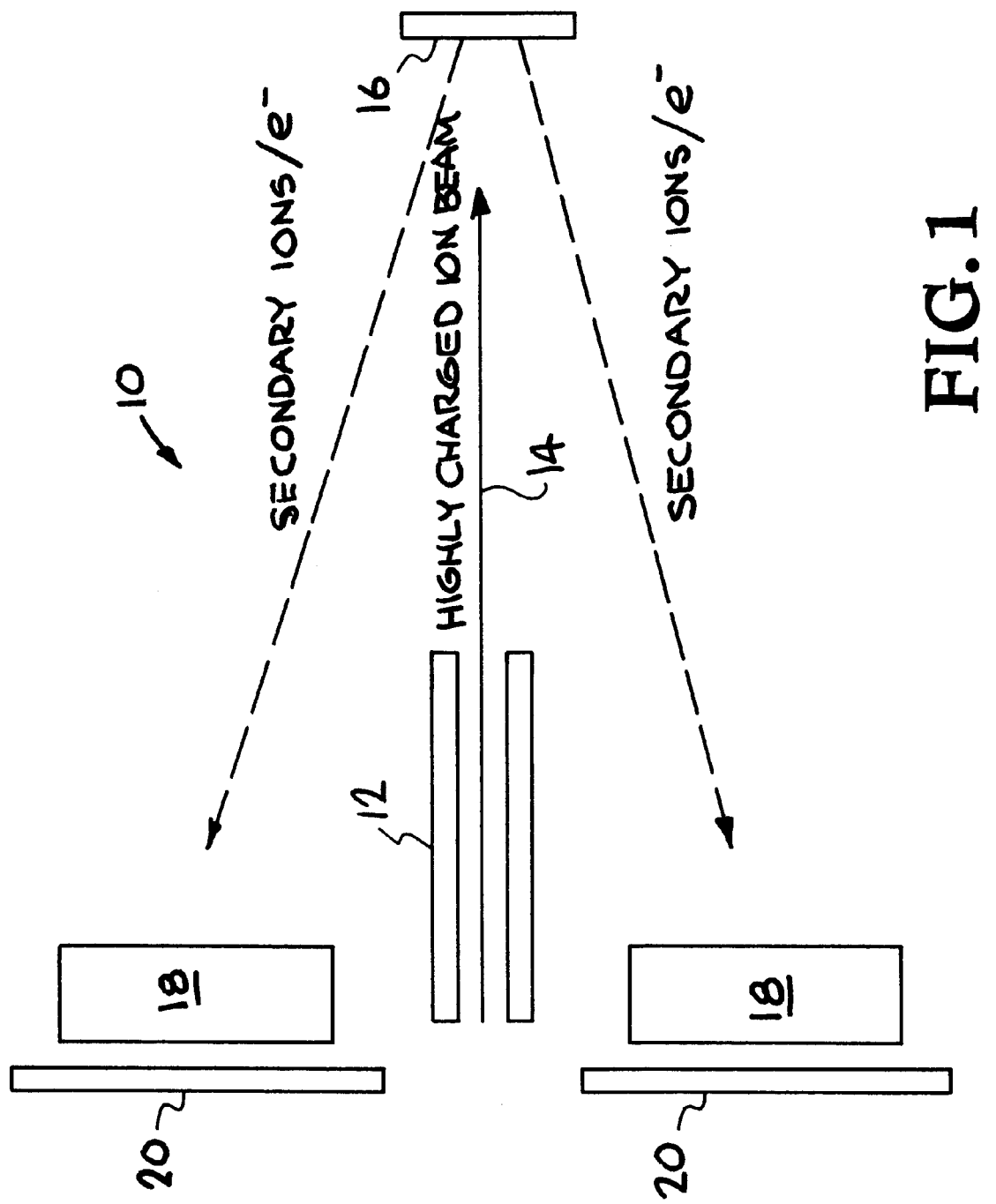
FIG. 1 shows a schematic diagram of the SIMS according to the present invention.

FIG. 1 shows a schematic diagram of the secondary ion mass spectrometer 10. The ion source 12 of highly charged ions produces a primary ion beam 14, which is directed onto a target surface 16. Secondary ions (and electrons) emanate from the target 16, and the ions are directed through a mass analyzer 18 to a microchannel plate detector 20.

The source 12 of highly charged ions is a compact (table top-sized) electron beam ion trap (EBIT) developed at Lawrence Livermore National Laboratory. The EBIT is the only currently available ion source capable of producing beams of slow, very highly charged ions. The charge, mass, and energy of this primary beam can be varied independently. Through the addition of ion extraction optics, the EBIT has developed into a versatile, novel ion source for slow velocity (about $10^5$ m/s) highly charged ions. Charge states of greater than one and up to 80+ can be selected. The initial charge states of highly charged ions are much larger than the mean equilibrium charge states that correspond to their low velocities ($v \leq 0.3\ v_{Bohr}$, $E_{kin} \leq 3$ keV/amu). Slow, highly charged ions are differentiated from fast ions of similar high charge states with velocities of $v > v_{Bohr}$, which are produced by charge state equilibration in gaseous or solid targets at relativistic energies (>100 MeV/amu). Highly charged incident ions have included the following: $O^{3,5,7+}$, $Ar^{16,18+}$, $Kr^{33+}$, $Xe^{12,15,16,20,21,24,25,27,28,30,32,35,36,40,44,48,51,52+}$, $Au^{44,48,52,56,58,60,64,69+}$, and $Th^{44,48,52,54,58,59,62,65,66,69,70,73,75+}$.

Highly charged ions carry a large amount of potential energy (100–300 keV per incident ion) when they interact with a surface. Individual highly charged ions, such as $Xe^{44+}$ or $Au^{69+}$, deposit an unusually high density (about 1 J/cm$^2$ or $10^{14}$ W/cm$^2$ per ion) of electronic excitations onto a nanometer sized surface area in less than 10 femtoseconds ($10^{-14}$ s). This extreme, localized excitation leads to electronic sputtering of the surface. Clusters and intact molecules from the surface give enhanced chemical structure information of the surface.

The electronically sputtered ions are detected by time-of-flight (TOF) mass spectrometry, where the mass-to-charge ratios of the secondaries are determined by the flight time from the target surface to the microchannel plate detector. High time resolution ($\leq 1$ ns) is achieved by "single ion triggering" on the emitted electron or proton pulse (as high as 200 electrons per ion for $Au^{69+}$) and stopping the time-to-digital converter with the secondary ion pulses.

Surface analysis is accomplished by determination of the mass and quantity of the elemental and molecular secondary ions removed from the target. (Secondary ions containing more than one atom are referred to as molecular ions.) The relationship between the signal intensity and the composition of the surface is determined by the relative sensitivity factor between the secondary ion in question and the target matrix ions.

Figure 2A:
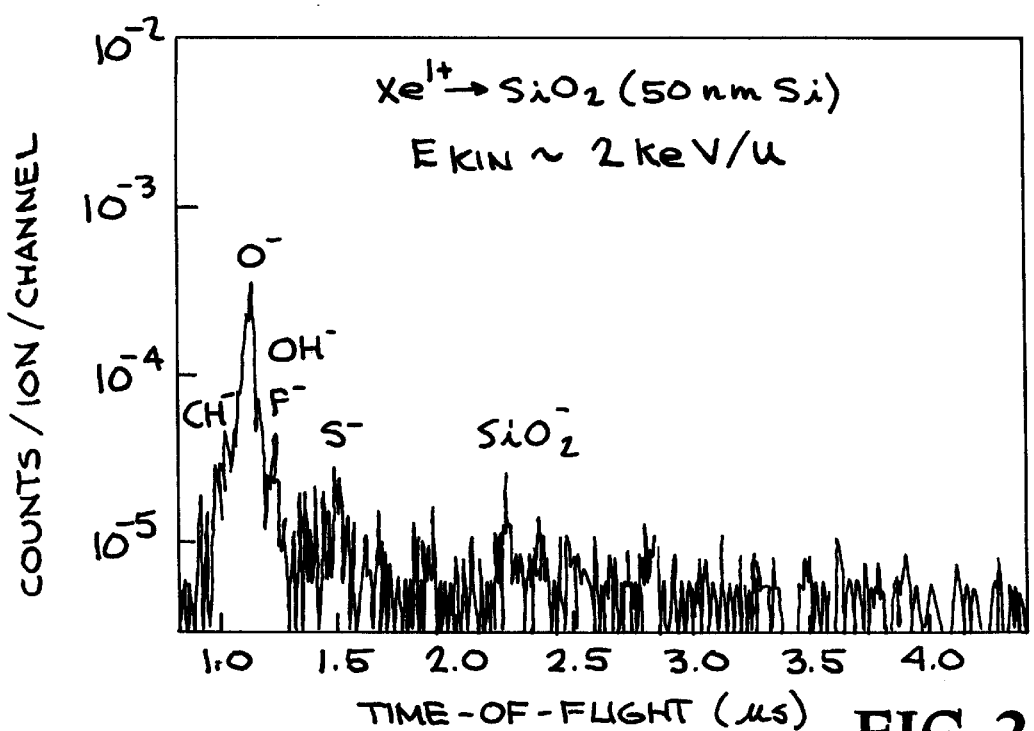
FIG. 2A shows sputtering by $Xe^{1+}$ using conventional time of flight mass spectrometry.
Figure 2B:
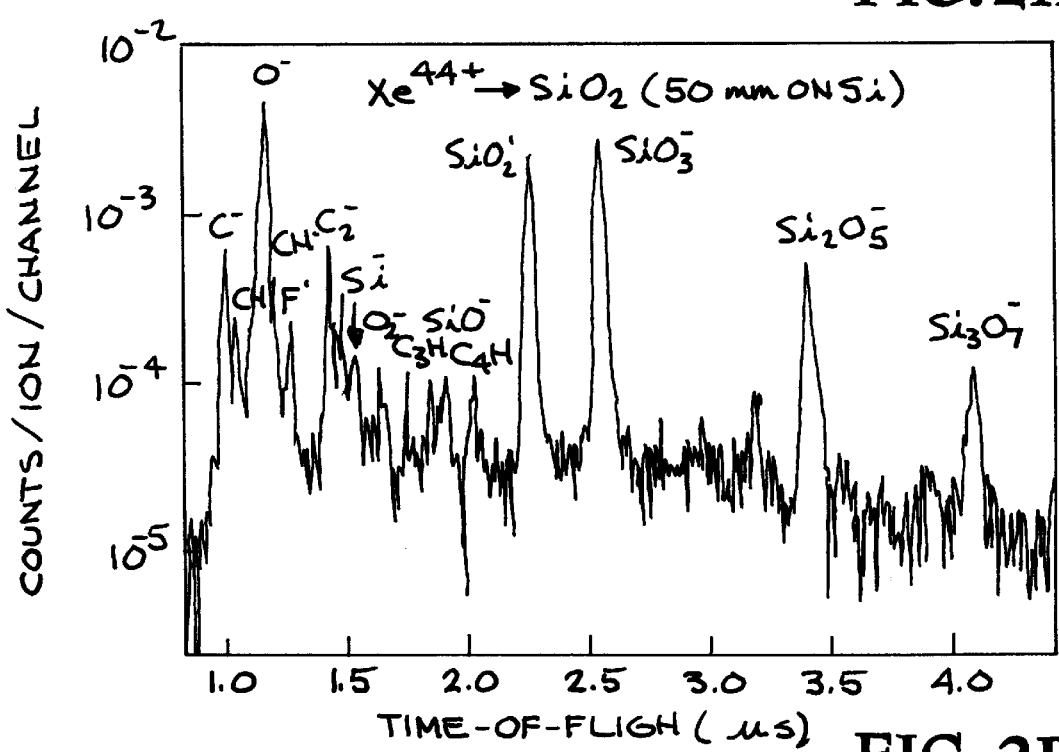
FIG. 2B shows sputtering by $Xe^{44\ +}$ using time of flight mass spectrometry according to the present invention.

The highly charged states of the ions cause a large increase (greater than 1000x) in secondary ion yield per incident ion, as well as the fraction ionized, which enhances sensitivity and reveals more chemical structure information than SIMS with singly charged ions. The ionized fraction increases as the charge (q) increases. Thus, sputtering with $Au^{69+}$ ions versus $Au^{1+}$ yields a >10-fold increase in the ionized fraction, which can be converted to a 10 to 50-fold increase in detection efficiency or material sensitivity. FIG. 2A shows collisional sputtering by $Xe^{1+}$ using time of flight mass spectrometry. FIG. 2B illustrates the dramatic increase in secondary ion yield using $Xe^{44+}$.

The present invention further improves on standard SIMS by applying coincidence counting. The high secondary ion yield and the secondary ion emission from a small area as a result of HCI-SIMS make the coincidence technique very powerful. In coincidence counting, the secondary ion stops are detected in coincidence with a start signal. There may be the additional requirement that a particular secondary ion is present. To detect secondary ions in coincidence with a required secondary ion within a reasonable time (e.g., hours vs. days), the secondary ion yield must be on the order produced by HCI-SIMS, i.e., 1–20 secondary ions per primary ion, in contrast with conventional SIMS, which on average provides less than 0.01 secondary ions per primary ion. Highly charged ion excitation is well suited to coincidence time-of-flight secondary ion mass spectrometry.

The EBIT source produces the beam of primary ions, from which ions of a specific mass-to-charge ratio are selected. The secondary yields are measured using TOF-SIMS. Fluxes of $\leq 10000$ ions per second may be used, where each TOF-SIMS cycle is triggered by secondary particles emitted from the target by the impact of an individual HCI under normal incidence. Typical accumulation times for the TOF-SIMS spectra are about ten minutes. The flight path for secondary ions is about 10 centimeters from the target surface to the detector.

High yields of electrons and protons may be used as start pulses for the TOF for negative and positive secondary ions, respectively. Start efficiencies are 100% for electron starts and between 10–80% for proton starts. Start signals and secondary ion stop signals are detected by the same annular microchannel plate detector. The TOF-SIMS spectra may be recorded with a multi-stop microchannel scaler. For coincidence measurements, the events may be collected in a list mode, i.e., the time of each start and its associated stops are recorded in a list. The data is then filtered for particular coincidence ions. An event, a start pulse and its associated stop pulses, is accepted if the coincidence ion is present, i.e., a stop pulse is detected in a particular time window, otherwise the event is discarded.

Figure 3:
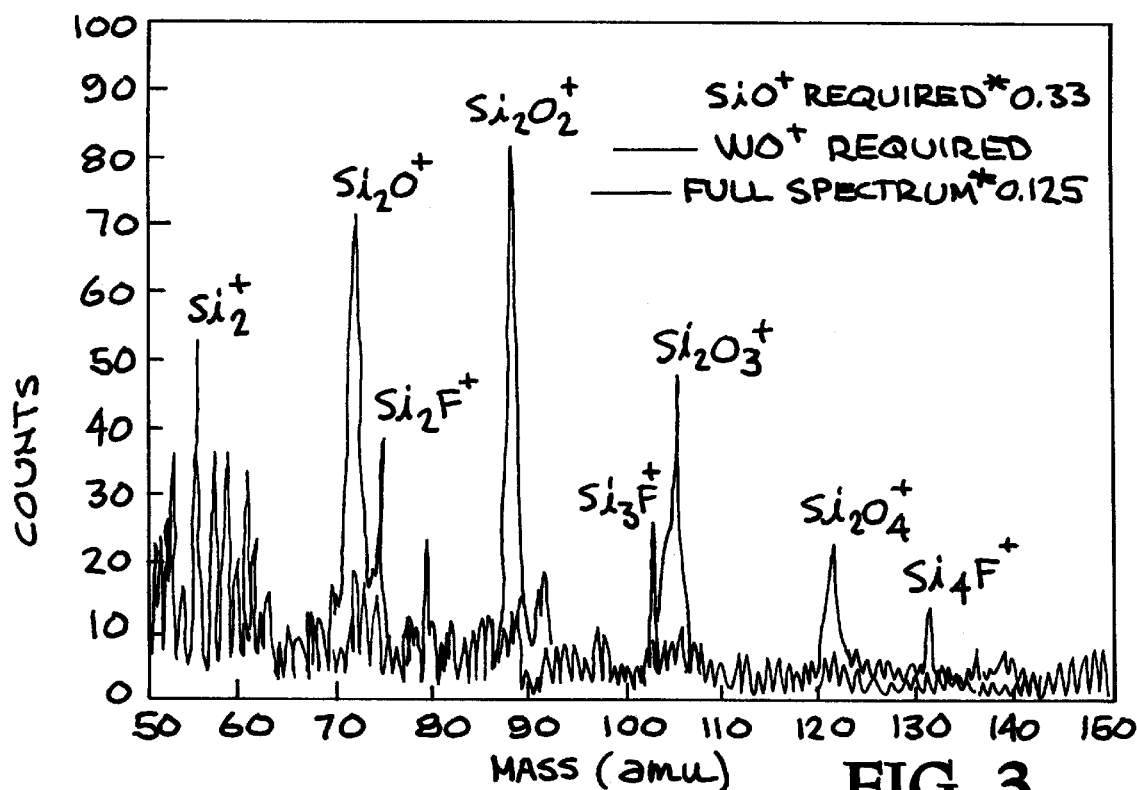
FIG. 3 shows the coincidence counting positive TOF-SIMS spectrum from a W/SiO$_2$/Si wafer with a $Th^{75+}$ primary beam according to the present invention.

FIG. 3 shows the coincidence counting positive TOF-SIMS spectrum from a W/SiO$_2$/Si test wafer with a $Th^{75+}$ primary beam with 262.5 keV incident energy. The sample is a patterned, thermally grown SiO$_2$/Si test wafer that was placed in a plasma CVD reactor for selective tungsten deposition. The SiO$_2$ layer is about one micron thick. Prior to deposition, the wafers were dipped in diluted HF (100:1) to eliminate the native oxide. Selective tungsten deposition (about 150–400 nm of α-tungsten) occurred via the reaction of WF$_6$ with Si$_2$H$_6$ at a wafer temperature of 150° C. The wafer was stored in air for several months before measurements were taken.

FIG. 3 shows the full spectrum, which is the sum of all the collected events, as well as the coincidence mass spectra selecting only events which have the secondary ion SiO$^+$ and WO$^+$. The spectra show that the Si$_2$O$_x$ series is highly correlated to the SiO$^+$ secondary ion and the Si$_x$F series is highly correlated to the WO$^+$ secondary ion. The degree of correlation can be quantitatively determined. Given that the tungsten is deposited from the reduction of WF$_6$ with disilane, the Si$_2$F$_6$ secondary ion impurity series is a by-product of the reduction that deposits with the tungsten.

Figure 4:
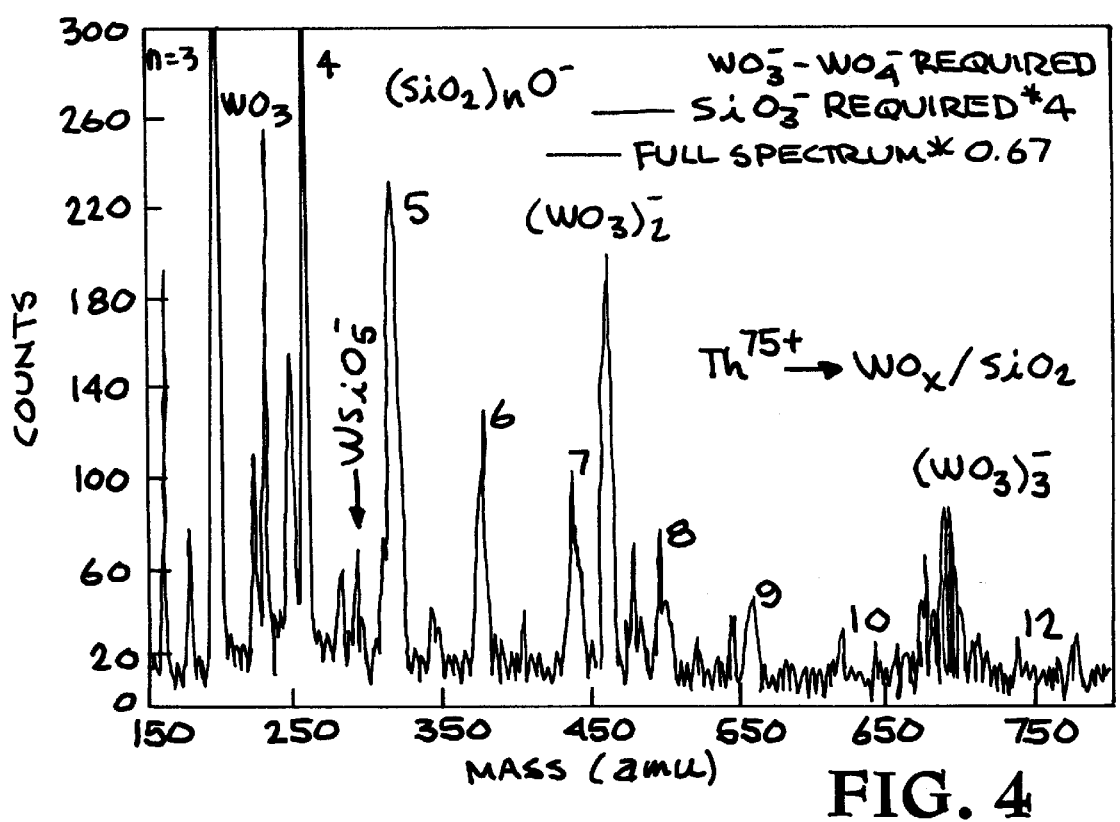
FIG. 4 shows the coincidence counting negative TOF-SIMS spectrum from a W/SiO$_2$/Si wafer with a $Th^{75+}$ primary beam according to the present invention.

FIG. 4 shows the coincidence counting negative TOF-SIMS spectrum from the W/SiO$_2$/Si wafer with the $Th^{75+}$ primary beam. The full spectrum is shown, which is the sum of all the collected sweeps, as well as the coincidence mass spectra selecting only sweeps which have the secondary ion SiO$_3^-$ and W0$_3$–WO$_4^-$. The coincidence technique allows the separation of the tungsten oxide duster series from the silicon dioxide cluster series, even though the cluster ions have many overlapping peaks at the mass resolution of a short, high transmission spectrometer. Thus, coincidence requirements in HCI-TOF-SIMS enhance the available information about nanoscopic chemical heterogeneity of the sample surface.

The foregoing description of preferred embodiments of the invention is presented for purposes of illustration and description and is not intended to be exhaustive or to limit the invention to the precise form disclosed. Many modifications and variations are possible in light of the above teaching.

What is claimed is:

1. A secondary ion mass spectrometer system, comprising:

a beam source comprising an electron beam ion trap for producing a primary ion beam of highly charged ions, wherein the beam is directed at a target surface to cause emission of sputtered secondary ions and electrons, from the target surface;

a mass analyzer into which are introduced the sputtered secondary ions; and a detector of the charged particles, wherein the sputtered secondary ions are detected in coincidence with a start signal and a selected secondary ion.

2. A secondary ion mass spectrometer as recited in claim 1, wherein the detector is a microchannel plate detector that detects the start signal and secondary ions.

3. A secondary ion mass spectrometer as recited in claim 1, wherein the primary beam produces highly charged ions having a charge state greater than one.

* * * * *